United States Patent
Hsu et al.

(10) Patent No.: US 6,719,997 B2
(45) Date of Patent: *Apr. 13, 2004

(54) TRANSDERMAL ADMINISTRATION OF PHARMACOLOGICALLY ACTIVE AMINES USING HYDROXIDE-RELEASING AGENTS AS PERMEATION ENHANCERS

(75) Inventors: Tsung-Min Hsu, San Diego, CA (US); Russell Macy, San Marcos, CA (US); Eric C. Luo, Plano, TX (US)

(73) Assignee: Dermatrends, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/738,395

(22) Filed: Dec. 14, 2000

(65) Prior Publication Data

US 2002/0018803 A1 Feb. 14, 2002

Related U.S. Application Data

(63) Continuation-in-part of application No. 09/607,892, filed on Jun. 30, 2000, now abandoned.

(51) Int. Cl.[7] .................................................. A61K 9/70
(52) U.S. Cl. ..................... 424/443; 424/445; 424/447; 424/448; 424/449; 424/514; 424/646; 424/725; 424/946; 424/947; 424/944
(58) Field of Search .................... 424/449, 443, 424/445, 447, 448, 514, 946, 947, 944; 514/646, 728

(56) References Cited

U.S. PATENT DOCUMENTS

| 3,028,429 | A | 4/1962 | Wilbert et al. |
| 4,289,749 | A | 9/1981 | Keith et al. |
| 4,789,547 | A | 12/1988 | Song et al. |
| 4,818,541 | A | 4/1989 | Sanderson |
| 4,837,027 | A | 6/1989 | Lee et al. |
| 4,885,312 | A | 12/1989 | Wurtman et al. |
| 5,019,594 | A | 5/1991 | Wurtman et al. |
| 5,021,457 | A | 6/1991 | Akin et al. |

(List continued on next page.)

FOREIGN PATENT DOCUMENTS

| CA | 2006425 | 6/1990 |
| EP | 0276561 | 8/1988 |
| EP | 0316065 | 5/1989 |
| EP | 0374725 | 6/1990 |
| EP | 0842662 | 5/1998 |
| FR | 2692145 | 12/1993 |
| JP | 6092843 | 4/1994 |
| WO | WO 82/00099 | 1/1982 |
| WO | WO 94/21271 | 9/1994 |
| WO | WO 97/47354 | 12/1997 |

OTHER PUBLICATIONS

Ito et al. (1991), "Skin Pretreatment and the Use of Transdermal Clonidine," *The American Journal of Medicine* 91(1A):42S–49S.

(List continued on next page.)

*Primary Examiner*—Thurman K. Page
*Assistant Examiner*—Konata M. George
(74) *Attorney, Agent, or Firm*—Reed & Eberle LLP; Dianne E. Reed; Shelley P. Eberle

(57) ABSTRACT

Methods, compositions and drug delivery systems are provided for the transdermal administration of a pharmacologically active amine. The active agent is administered with a hydroxide-releasing agent that serves as a permeation enhancer. Exemplary hydroxide-releasing agents are inorganic hydroxides, inorganic oxides, and alkali metal or alkaline earth metal salts of weak acids. Inorganic hydroxides include, for example, ammonium hydroxide, alkali metal hydroxides and alkaline earth metal hydroxides, such as sodium hydroxide, calcium hydroxide, potassium hydroxide, magnesium hydroxide, and the like.

77 Claims, 2 Drawing Sheets

U.S. PATENT DOCUMENTS

| | | |
|---|---|---|
| 5,071,657 A | 12/1991 | Oloff et al. |
| 5,096,712 A | 3/1992 | Wurtman |
| 5,260,073 A | 11/1993 | Phipps |
| 5,422,118 A | 6/1995 | Brown et al. |
| 5,462,744 A | 10/1995 | Gupte et al. |
| 5,474,783 A | 12/1995 | Miranda et al. |
| 5,498,417 A | 3/1996 | Lhila et al. |
| 5,534,496 A | 7/1996 | Lee et al. |
| 5,573,778 A | 11/1996 | Therriault et al. |
| 5,817,332 A | 10/1998 | Urtti et al. |
| 5,830,497 A | 11/1998 | Yamanaka et al. |
| 5,879,690 A | 3/1999 | Perricone |
| 5,985,317 A | 11/1999 | Venkateshwaran et al. |
| 5,985,856 A | 11/1999 | Stella et al. |
| 5,985,860 A | 11/1999 | Toppo |
| 5,989,586 A | 11/1999 | Hsu et al. |
| 5,990,179 A | 11/1999 | Gyory et al. |
| 5,993,851 A | 11/1999 | Foldvari |
| 6,004,577 A | 12/1999 | Murdock |
| 6,019,988 A | 2/2000 | Parab et al. |
| 6,019,997 A | 2/2000 | Scholz et al. |
| 6,139,866 A | 10/2000 | Chono et al. |
| 6,174,546 B1 | 1/2001 | Therriault et al. |
| 6,204,268 B1 | 3/2001 | Scarborough et al. |
| 6,270,793 B1 * | 8/2001 | Van Dyke et al. .......... 424/443 |

OTHER PUBLICATIONS

U.S. patent application Ser. No. 09/569,889, Luo et al., filed May 11, 2000.

Scherzinger et al. (1990), "Steady State Pharmacokinetics and Dose–Proportionality of Phenylpropanolamine in Healthy Subjects," *J. Clin. Pharmacol.* 30(4):372–377.

U.S. patent application Ser. No. 09/607892, Hsu et al., filed Jun. 30, 2000.

Andrews et al. (1980), "Nitrosation and Mutagenicity of Some Amine Drugs," *Toxicology and Applied Pharmacology 52:*237–244.

Andrews et al. (1984), "Mutagenicity of Amine Drugs and Their Products of Nitrosation," *Mutation Research 135:*105–108.

Aungst et al. (1990), "Contributions of Drug Solubilization, Partitioning, Barrier Disruption, and Solvent Permeation to the Enhancement of Skin Permeation of Various Compounds with Fatty Acids and Amines," *Pharmaceutical Research* 7(7):712–718.

Greenwald et al. (1999), "Drug Delivery Systems Employing 1,4– or 1,6–Elimination: Poly(Ethylene Glycol) Prodrugs of Amine–Containing Compounds," *J. Med. Chem.* 42(18):3657–3667.

Hiripi et al. (1994), "Characterization of Tyramine and Octopamine Receptors in the Insect (*Locusta Migratoria Migratorioides*) Brain," *Brain Research 633*:119–126.

Matsui et al. (1995), "Structure–Activity Relationships of Alkylamines that Inhibit Rat Liver Hydroxysteroid Sulfotransferase Activities In Vitro," *Biochemical Pharmacology 49*(5):739–741.

Maurer–Spurej et al. (1999), "Factors Influencing Uptake and Retention of Amino–Containing Drugs in Large Unilamellar Vesicles Exhibiting Transmembrane pH Gradients," *Biochimica et Biophysica Acta 1416*:1–10.

Sharp et al. (1992), "Inhibition of Human and Rabbit Liver Steroid and Xenobiotic UDP–Glucuronosyltransferases by Tertiary Amine Drugs–Implications for Adverse Drug Reactions," *Xenobiotica* 22(1):13–25.

Tong et al. (1991), "Structural Effects on the Binding of Amine Drugs with Diphenylmethyl Functionality to Cyclodextrins. II. A Molecular Modeling Study," *Pharmaceutical Research* 8(10):1307–1312.

Wang et al. (1998), "Coumarin–Based Prodrugs. Part 3: Structural Effects on the Release Kinetics of Esterase–Sensitive Produgs of Amines," *Bioorganic and Medicinal Chemistry* 6:417–426.

Worland et al. (1981), "Effect of Basic Amine Drugs on the Metabolism of Angiotensin I in Rat Lung Homongenates," *J. Pharm. Pharmacol.* 33:794–795.

* cited by examiner

TRANSDERMAL ADMINISTRATION OF PHARMACOLOGICALLY ACTIVE AMINES USING HYDROXIDE-RELEASING AGENTS AS PERMEATION ENHANCERS

CROSS-REFERENCE TO RELATED APPLICATIONS

This is a continuation-in-part of U.S. Ser. No. 09/607,892, filed Jun. 30, 2000, now abandoned the disclosure of which is incorporated by reference.

TECHNICAL FIELD

This invention relates generally to the topical and transdermal administration of pharmacologically active agents, and more particularly relates to methods, drug delivery systems and pharmaceutical compositions for transdermal administration of pharmologically active amines.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug. Side effects typically associated with oral administration may be substantially avoided, and the likelihood of both patient acceptance and patient compliance is significantly improved.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing which creates in most cases a substantially impermeable barrier to drug penetration. With many drugs, the rate of permeation through the skin is extremely low without the use of some means to enhance the permeability of the skin.

In order to increase the rate at which a drug penetrates through the skin, then, various approaches have been followed, each of which involves the use of either a chemical penetration enhancer or a physical penetration enhancer. Physical enhancement of skin permeation includes, for example, electrophoretic techniques such as iontophoresis. The use of ultrasound (or "phonophoresis") as a physical penetration enhancer has also been researched. Chemical enhancers are compounds that are administered along with the drug (or in some cases the skin may be pretreated with a chemical enhancer) in order to increase the permeability of the stratum corneum, and thereby provide for enhanced penetration of the drug through the skin. Ideally, such chemical penetration enhancers (or "permeation enhancers," as the compounds are referred to herein) are compounds that are innocuous and serve merely to facilitate diffusion of the drug through the stratum corneum.

Various compounds for enhancing the permeability of skin are known in the art and described in the pertinent texts and literature. Compounds that have been used to enhance skin permeability include: the sulfoxides dimethylsulfoxide (DMSO) and decylmethylsulfoxide ($C_{10}MSO$); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclazacycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid. *Percutaneous Penetration Enhancers*, eds. Smith et al. (CRC Press, 1995) provides an excellent overview of the field and further background information on a number of chemical and physical enhancers.

Although many chemical permeation enhancers are known, there is an ongoing need for enhancers that are highly effective in increasing the rate at which a drug permeates the skin, do not result in skin damage, irritation, sensitization, or the like, and can be used to effect transdermal delivery of even high molecular weight drugs such as steroid drugs. It has now been discovered that hydroxide-releasing agents are highly effective permeation enhancers, even when used without coenhancers, provide all of the aforementioned advantages relative to known permeation enhancers. Furthermore, in contrast to conventional enhancers, transdermal administration of drugs with hydroxide-releasing agents as permeation enhancers, employed at the appropriate levels, does not result in systemic toxicity.

The present invention is directed to the transdermal administration of pharmacologically active amines. Many amine drugs exhibit low transdermal flux rate, particularly when the drug is in the form of an acid addition salt. For example, racemic phenylpropanolamine (i.e., (±)-phenylpropanolamine, a mixture of (−)-norephedrine and (+)-norephedrine) is only 16 $\mu g/cm^2/hr$. See, for example, U.S. Pat. No. 4,818,541. Scopolamine, a well known anti-emetic agent and anti-nauseant, also exhibits relatively low transdermal flux, necessitating application to a very specific skin area. Numerous other amine drugs are also known to be problematic in this regard.

Furthermore, many amine drugs are available commercially only in the form of an acid addition salt. When the agents are to be administered transdermally, it is generally necessary to convert the acid addition salt to the free amine base before incorporation into a transdermal delivery device. The method of the '541 patent is representative of such a procedure, in that the patent requires neutralization of phenylpropanolamine hydrochloride (i.e., conversion to the free base), the commercially available form of the drug, before incorporation into a transdermal drug delivery system.

Accordingly, there is a need in the art for a way to transdermally administer a pharmacologically active amine at a transdermal flux rate that is high enough to ensure that physiologically effective blood levels of the drug are obtained. It would also be desirable to provide a transdermal system wherein it is unnecessary to convert an acid addition salt to the base form of the drug prior to patch manufacture. It has now been discovered that use of hydroxide-releasing agents as permeation enhancers fulfills both of the aforementioned functions.

SUMMARY OF THE INVENTION

It is thus a primary object of the invention to address the above-described need in the art by providing drug delivery systems, pharmaceutical formulations and methods for the transdermal administration of pharmacologically active amines.

It is another object of the invention to provide a method for treating conditions, disorders or diseases that are responsive to administration of a pharmacologically active amine by transdermally administering the amine in conjunction with a hydroxide-releasing agent as a permeation enhancer.

It is still another object of the invention to provide a method for transdermally administering a pharmacologically active amine at a flux that is effective to provide for physiologically effective blood levels of the drug.

It is yet another object of the invention to provide a transdermal drug delivery system for administration of a pharmacologically active amine such that a therapeutically effective skin flux is achieved.

It is a further object of the invention to provide a chemical composition containing a pharmacologically active amine, formulated for transdermal drug delivery.

It is still a further object of the invention to provide a method for manufacturing a transdermal drug delivery system wherein an acid addition salt of a pharmacologically active amine is converted to the base form of the drug during system manufacture.

Additional objects, advantages and novel features of the invention will be set forth in part in the description which follows, and in part will become apparent to those skilled in the art upon examination of the following, or may be learned by practice of the invention.

In one aspect of the invention, then, a method is provided for increasing the rate at which a pharmacologically active amine permeates through the body surface of a patient. The method involves administering the amine to a predetermined area of the patient's body surface in combination with a hydroxide-releasing agent in a predetermined amount effective to enhance the flux of the amine through the body surface without causing damage thereto. The predetermined amount of the hydroxide-releasing enhancer is preferably an amount effective to provide a pH at the body surface in the range of about 8.0 to 13, preferably about 8.0 to 11.5, more preferably about 8.5 to 11.5, during drug administration. If a skin patch is used, this is the preferred pH at the interface between the basal surface of the patch (i.e., the skin-contacting or mucosa-contacting surface of the patch) and the body surface. The optimal amount (or concentration) of any one hydroxide-releasing agent will, however, depend on the specific hydroxide-releasing agent, i.e., on the strength or weakness of the base, its molecular weight, and other factors as will be appreciated by those of ordinary skill in the art of transdermal drug delivery. This optimal amount may be determined using routine experimentation to ensure that the pH at the body surface is within the aforementioned ranges, i.e., in the range of about 8.0 to 13, preferably about 8.0 to 11.5, more preferably about 8.5 to 11.5. A conventional transdermal drug delivery device or "patch" may be used to administer the active agent, in which case the drug and hydroxide-releasing agent are generally present in a drug reservoir or reservoirs. However, the drug and hydroxide-releasing agent may also be administered to the body surface using a liquid or semisolid formulation. Alternatively, or in addition, the body surface may be pretreated with the enhancer, e.g., treated with a dilute solution of the hydroxide-releasing agent prior to transdermal drug administration. Such a solution will generally be comprised of a protic solvent (e.g., water or alcohol) and have a pH in the range of about 8.0 to 13, preferably about 8.0 to 11.5, more preferably about 8.5 to 11.5.

In a related aspect of the invention, a composition of matter is provided for delivering a pharmacologically active amine through a body surface using a hydroxide-releasing agent as a permeation enhancer. Generally, the formulation comprises (a) a therapeutically effective amount of the pharmacologically active amine, (b) a hydroxide-releasing agent in an amount effective to enhance the flux of the drug through the body surface without causing damage thereto, and (c) a pharmaceutically acceptable carrier suitable for topical or transdermal drug administration. The composition may be in any form suitable for application to the body surface, and may comprise, for example, a cream, lotion, solution, gel, ointment, paste or the like, and/or may be prepared so as to contain liposomes, micelles, and/or microspheres. The composition may be directly applied to the body surface or may involve use of a drug delivery device. In either case, it is preferred although not essential that water be present in order for the hydroxide-releasing agent to generate hydroxide ions and thus enhance the flux of the active agent through the patient's body surface. Thus, a formulation or drug reservoir may be aqueous, i.e., contain water, or may be nonaqueous and used in combination with an occlusive overlayer so that moisture evaporating from the body surface is maintained within the formulation or transdermal system during drug administration.

In another aspect of the invention, a drug delivery system is provided for the topical or transdermal administration of a pharmacologically active amine using a hydroxide-releasing agent as a permeation enhancer. The system will generally comprise: at least one drug reservoir containing the drug and the hydroxide-releasing agent in an amount effective to enhance the flux of the drug through the body surface without causing damage thereto; a means for maintaining the system in drug and enhancer transmitting relationship to the body surface; and a backing layer that serves as the outer surface of the device during use. The backing layer may be occlusive or nonocclusive, although it is preferably occlusive. The drug reservoir may be comprised of a polymeric adhesive, which may serve as the basal surface of the system during use and thus function as the means for maintaining the system in drug and enhancer transmitting relationship to the body surface. The drug reservoir may also be comprised of a hydrogel, or it may be a sealed pouch within a "patch"-type structure wherein the drug and hydroxide-releasing agent are present in the pouch as a liquid or semi-solid formulation.

BRIEF DESCRIPTION OF THE DRAWINGS

FIG. 3 is a graph illustrating the cumulative amount of racemic phenylpropanolamine permeated from matrix patches as described in Example 3.

FIG. 4 is a graph illustrating the cumulative amount of racemic phenylpropanolamine permeated from matrix patches as described in Example 4.

FIG. 5 is a graph illustrating the cumulative amount of racemic phenylpropanolamine permeated from matrix patches as described in Example 5.

DETAILED DESCRIPTION OF THE INVENTION

Definitions and Overview

Figure 1:
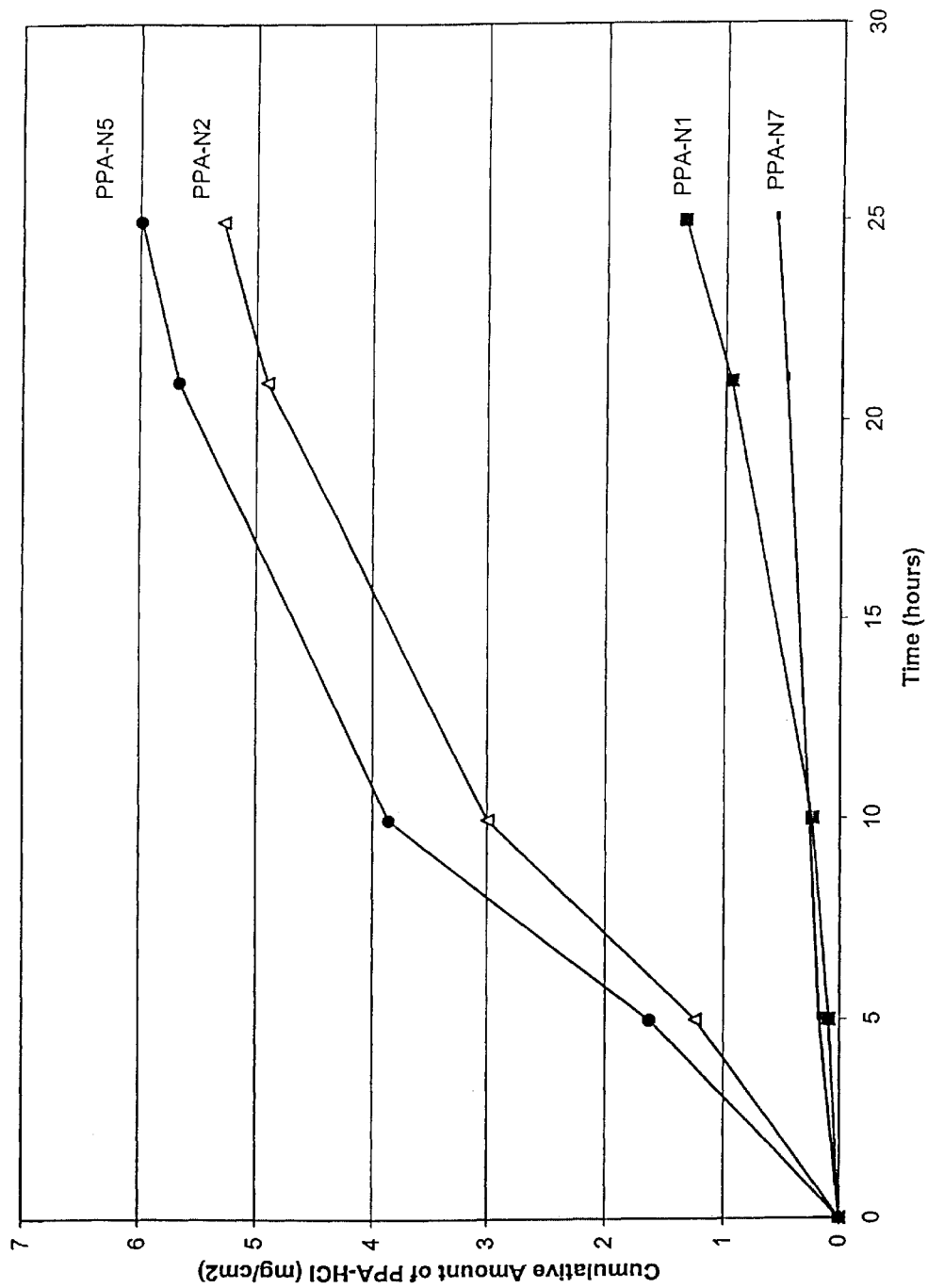
FIG. 1 is a graph illustrating the cumulative amount of racemic phenylpropanolamine permeated from matrix patches as described in Example 1.

Before describing the present invention in detail, it is to be understood that this invention is not limited to specific drug delivery systems, device structures, enhancers or carriers, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "pharmacologically active amine" includes a mixture of two or more such amines, reference to "an enhancer" includes mixtures of two or more enhancers, reference to "a hydroxide-releasing agent" includes mixtures of hydroxide-releasing agents, and the like.

In describing and claiming the present invention, the following terminology will be used in accordance with the definitions set out below.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a patient, as the term is used herein, thus encompasses both prevention of a disorder in a predisposed individual and treatment of the disorder in a clinically symptomatic individual.

The term "hydroxide-releasing agent" as used herein is intended to mean an agent that releases free hydroxide ions in an aqueous environment. The agent may contain hydroxide ions and thus release the ions directly (e.g., an alkali metal hydroxide), or the agent may be one that is acted upon chemically in an aqueous environment to generate hydroxide ions (e.g., a metal carbonate).

The terms "active agent," "drug" and "pharmacologically active agent" are used interchangeably herein to refer to a chemical material or compound that induces a desired effect, and include agents that are therapeutically effective, prophylactically effective, or cosmetically effective. Also included are derivatives and analogs of those compounds or classes of compounds specifically mentioned which also induce the desired effect. The active agents herein are amines.

The term "amine" is used herein to refer to primary, secondary and tertiary amines, as the term is conventionally used, and is also intended to encompass other nitrogen-containing compounds such as aromatic and non-aromatic nitrogen-containing heterocycles, azo compounds, and imines. Thus, the term "amine" is used to include nitrogen-containing bases as well as conventional amines per se.

"By therapeutically effective" amount is meant a nontoxic but sufficient amount of an active agent to provide the desired therapeutic effect.

By "transdermal" drug delivery is meant administration of a drug to the skin surface of an individual so that the drug passes through the skin tissue and into the individual's blood stream, thereby producing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream. Unless otherwise stated or implied, the terms "topical drug administration" and "transdermal drug administration" are used interchangeably.

The term "topical administration" is used in its conventional sense to mean delivery of a topical drug of a pharmacologically active agent to the skin or mucosa, as in, for example, the treatment of various skin disorders. Topical drug administration, in contrast to transdermal administration, provides a local rather than a systemic effect. Unless otherwise stated or implied, the terms "topical drug administration" and "transdermal drug administration" are used interchangeably.

The term "body surface" is used to refer to skin or mucosal tissue.

By "predetermined area" of skin or mucosal tissue, which refers to the area of skin or mucosal tissue through which PPA is delivered, is intended a defined area of intact unbroken living skin or mucosal tissue. That area will usually be in the range of about 5 cm$^2$ to about 200 cm$^2$, more usually in the range of about 5 cm$^2$ to about 100 cm$^2$, preferably in the range of about 20 cm$^2$ to about 60 cm$^2$. However, it will be appreciated by those skilled in the art of drug delivery that the area of skin or mucosal tissue through which the drug is administered may vary significantly, depending on patch configuration, dose, and the like.

"Penetration enhancement" or "permeation enhancement" as used herein relates to an increase in the permeability of the skin or mucosal tissue to the selected pharmacologically active amine, i.e., so that the rate at which the amine permeates therethrough (i.e., the "flux" of the agent through the body surface) is increased relative to the rate that would be obtained in the absence of permeation enhancement. The enhanced permeation effected through the use of such enhancers can be observed by measuring the rate of diffusion of drug through animal or human skin using, for example, a Franz diffusion apparatus as known in the art and as employed in the Examples herein.

An "effective" amount of a permeation enhancer is meant a nontoxic, nondamaging but sufficient amount of the enhancer to provide the desired increase in skin permeability and, correspondingly, the desired depth of penetration, rate of administration, and amount of drug delivered.

"Carriers" or "vehicles" as used herein refer to carrier materials suitable for transdermal drug administration. Carriers and vehicles useful herein include any such materials known in the art which is nontoxic and does not interact with other components of the composition in a deleterious manner.

The term "aqueous" refers to a formulation or drug delivery system that contains water or that becomes water-containing following application to the skin or mucosal tissue.

The term "racemic phenylpropanolamine" as used herein refers to a mixture of two or more of the four isomers of phenylpropanolamine, i.e., (+)-norephedrine, (−)-norephedrine, (+)-norpseudoephedrine, and (−)-norpseudoephedrine. Generally, however, the term refers to (±)-phenylpropanolamine, i.e., a racemic mixture of (−)-norephedrine and (+)-norephedrine. Phenylpropanolamine is generally although not necessarily administered in uncharged (electronically neutral) form, wherein the amine group of the molecule exists in free base form, i.e., as an —$NH_2$ moiety.

Accordingly, the invention pertains to a method, composition and drug delivery system for increasing the rate at which a pharmacologically active amine permeates through the body surface of a patient at a rate that is effective to result in therapeutically effective blood levels. The method involves administering the agent to a predetermined area of the patient's body surface in combination with a hydroxide-releasing agent in an amount effective to enhance the flux of the amine through the body surface without causing damage thereto.

Thus, the present method of transdermally delivering the pharmacologically active amine may vary, but necessarily involves application of a composition containing the pharmacologically active amine to a predetermined area of the skin or mucosal tissue for a period of time sufficient to provide an effective blood level of drug for a desired period of time. The method may involve direct application of the composition as an ointment, gel, cream, or the like, or may involve use of a drug delivery device as taught in the art, e.g., in commonly assigned U.S. Pat. Nos. 4,915,950, 4,906,463, 5,091,186 or 5,246,705, or as described below.

The Hydroxide-releasing Agent

The "hydroxide-releasing agent" is a chemical compound that releases free hydroxide ions in the presence of an aqueous fluid. The aqueous fluid may be natural moisture at the skin surface, or a patch or composition that is used may contain added water, and/or be used in connection with an occlusive backing. Similarly, any liquid or semisolid formulation that is used is preferably aqueous or used in conjunction with an overlayer of an occlusive material.

Any hydroxide-releasing agent may be used provided that the compound releases free hydroxide ions in the presence of an aqueous fluid. Examples of suitable hydroxide-releasing agents include, but are not limited to, inorganic hydroxides, inorganic oxides, and alkali metal or alkaline earth metal salts of weak acids. Inorganic hydroxides include, for example, ammonium hydroxide, alkali metal hydroxide and alkaline earth metal hydroxides, such as sodium hydroxide, calcium hydroxide, potassium hydroxide, magnesium hydroxide, and the like. Inorganic oxides include, for example, magnesium oxide, calcium oxide, and the like. Metal salts of weak acids include, for example, sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), ammonium phosphate (dibasic), and the like. Preferred hydroxide-releasing agents are metal hydroxides such as sodium hydroxide and potassium hydroxide.

It is important that the amount of hydroxide-releasing agent in any patch or formulation is optimized so as to increase the flux of the drug through the body surface while minimizing any possibility of skin damage. In general, this means that the pH at the body surface in contact with a formulation or drug delivery system of the invention (i.e., the interface between the body surface and the formulation or delivery system) should be in the range of approximately 8.0 to 13, preferably about 8.0 to 11.5, more preferably about 8.5 to 11.5. This will typically although not necessarily mean that the pH of the formulation or the drug composition contained within a delivery system will be in the range of approximately 8.0 to 13, preferably about 8.0 to 11.5, more preferably about 8.5 to 11.5.

For inorganic hydroxides, the amount of hydroxide-releasing agent will typically represent about 0.5 wt. % to 4.0 wt. %, preferably about 0.5 wt. % to 3.0 wt. %, more preferably about 0.75 wt. % to 2.0 wt. % and optimally about 1.0 wt. %, of a topically applied formulation or of a drug reservoir of a drug delivery system, or "patch." The aforementioned amount applies to formulations and patches in which the active agent is (1) an uncharged molecule, i.e., the amine drug is in nonionized, free base form, and (2) there are no additional species in the formulation or patch that could react with or be neutralized by the inorganic hydroxide. For formulations and patches in which the amine drug is in the form of an acid addition salt, and/or wherein there are additional species in the formulations or systems that can be neutralized by or react with the hydroxide-releasing agent (i.e., acidic inactive ingredients), the amount of inorganic hydroxide will be the total of (1) the amount necessary to neutralize the acid addition salt and/or other base-neutralizable species, plus (2) about 0.5 wt. % to 4.0 wt. %, preferably about 0.5 wt. % to 3.0 wt. %, more preferably about 0.75 wt. % to 2.0 wt. % and optimally about 1.0 wt. %, of the formulation or drug reservoir. That is, for an acid addition salt of the amine drug, the inorganic hydroxide should be present in an amount just sufficient to neutralize the salt, plus an additional amount (i.e., about 0.5 wt. % to 4.0 wt. %, preferably about 0.5 wt. % to 3.0 wt. %, more preferably about 0.75 wt. % to 2.0 wt. % and optimally about 1.0 wt. %) to enhance the flux of the drug through the skin or mucosal tissue. For patches, the aforementioned percentages are given relative to the total dry weight of the formulation components and the adhesive, gel or liquid reservoir.

For other hydroxide-releasing agents such as inorganic oxides and metal salts of weak acids, the amount of hydroxide-releasing agent in the formulation or drug delivery system may be substantially higher, as high as 20 wt. %, in some cases as high as 25 wt. % or higher, but will generally be in the range of approximately 2 wt. % to 20 wt. %.

Still greater amounts of hydroxide-releasing agent may be used by controlling the rate and/or quantity of release of the hydroxide-releasing agent preferably during the drug delivery period itself.

However, for all hydroxide-releasing agents herein, the optimum amount of any particular agent will depend on the strength or weakness of the base, the molecular weight of the base, and other factors such as the number of ionizable sites in the drug administered and any other acidic species in the formulation or patch. One skilled in the art may readily determine the optimum amount for any particular agent by ensuring that a formulation or drug delivery system should in all cases be effective to provide a pH at the skin surface in the range of about 8.0 to 13, preferably in the range of about 8.0 to 11.5, more preferably in the range of about 8.5 to 11.5, during application to reach the desired pH at the body surface. This in turn ensures that the degree of enhancement is optimized while the possibility of damage to the body surface is eliminated or at least substantially minimized.

The Active Agent

The active agent administered may be any amine compound that is suitable for topical, transdermal or transmucosal delivery and induces a desired local or systemic effect. Such substances include the broad classes of compounds normally delivered through body surfaces and membranes, including skin. In general, this includes: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antineoplastic agents; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids; sympathomimetics; tranquilizers; and vasodilators including general coronary, peripheral and cerebral. The pharmacologically active amine may be one that is cosmetically or "cosmeceutically" effective rather than pharmacologically active. Such agents include, for example, compounds that can reduce the appearance of aging or photodamaged skin.

The pharmacologically active agent may be a primary amine, a secondary amine, or a tertiary amine, or it may be an aromatic or non-aromatic nitrogen-containing heterocycle, an azo compound, an imine, or a combination of any of the foregoing.

Examples of specific primary amines include, but are not limited to, amphetamine, norepinephrine, phenylpropanolamine (including any of the four isomers, individually or in combination, i.e., (+)-norephedrine, (−)-norephedrine, (+)-norpseudoephedrine, and (−)-norpseudoephedrine), and pyrithiamine.

Examples of secondary and tertiary amines include, but are not limited to, amiodarone, amitryptyline, azithromycin, benzphetamine, bromopheniramine, chlorambucil, chloroprocaine, chloroquine, chlorpheniramine, chlorothen, chlorpromazine, cinnarizine, clarthromycin, clomiphene, cyclobenzaprine, cyclopentolate, cyclophosphamide, dacarbazine, demeclocycline, dibucaine, dicyclomine, diethylproprion, diltiazem, dimenhydrinate, diphenhydramine, diphenylpyraline, disopyramide, doxepin, doxycycline, doxylamine, dypyridame, ephedrine, epinephrine, ethylene diamine tetraacetic acid (EDTA), erythromycin, flurazepam, gentian violet, hydroxychloroquine, imipramine, isoproterenol, isothipendyl, levomethadyl, lidocaine, loxarine, mechlorethamine, melphalan, methadone, methafurylene, methapheniline, methapyrilene, methdilazine, methotimeperazine, methotrexate, metoclopramide, minocycline, naftifine, nicardipine, nicotine, nizatidine, orphenadrine, oxybutin, oxytetracycline, phenindamine, pheniramine, phenoxybenzamine, phentolamine, phenylephrine, phenyltoloxamine, procainamide, procaine, promazine, promethazine, proparacaine, propoxycaine, propoxyphene, pyrilamine, ranitidine, scopolamine, tamoxifen, terbinafine, tetracaine, tetracycline, thonzylamine, tranadol, triflupromazine, trimeprazine, trimethylbenzamide, trimipramine, trlpelennamine, troleandomycin, uracil mustard, verapamil and vonedrine.

Examples of non-aromatic heterocyclic amines include, but are not limited to, alprazolam, amoxapine, arecoline, astemizole, atropine, azithromycin, benzapril, benztropine, beperiden, bupracaine, buprenorphine, buspirone, butorphanol, caffeine, capriomycin, ceftriaxone, chlorazepate, chlorcyclizine, chlordiazepoxide, chlorpromazine, chlorthiazide, ciprofloxacin, cladarabine, clemastine, clemizole, clindamycin, clofazamine, clonazepam, clonidine, clozapine, cocaine, codeine, cyclizine, cyproheptadine, dacarbzine, dactinomycin, desipramine, diazoxide, dihydroergotamine, diphenidol, diphenoxylate, dipyridamole, doxapram, ergotamine, estazolam, famciclovir, fentanyl, flavoxate, fludarabine, fluphenazine, flurazepam, fluvastin, folic acid, ganciclovir, granisetron, guanethidine, halazepam, haloperidol, homatropine, hydrocodone, hydromorphone, hydroxyzine, hyoscyamine, imipramine, itraconazole, keterolac, ketoconazole, levocarbustine, levorphone, lincomycin, lomefloxacin, loperamide, lorazepam, losartan, loxapine, mazindol, meclizine, meperidine, mepivacaine, mesoridazine, methdilazine, methenamine, methimazole, methotrimeperazine, methysergide, metronidazole, midazolam, minoxidil, mitomycin c, molindone, morphine, nafzodone, nalbuphine, naldixic acid, nalmefene, naloxone, naltrexone, naphazoline, nedocromil, nicotine, norfloxacin, ofloxacin, ondansetron, oxazepam, oxycodone, oxymetazoline, oxymorphone, pemoline, pentazocine, pentostatin, pentoxyfylline, perphenazine, phentolamine, physostigmine, pilocarpine, pimozide, pramoxine, prazosin, prochlorperazine, promazine, promethazine, pyrrobutamine, quazepam, quinidine, quinine, rauwolfia alkaloids, riboflavin, rifabutin, risperidone, rocuronium, scopalamine, sufentanil, tacrine, temazepam, terazosin, terconazole, terfenadine, tetrahydrazoline, thiordazine, thiothixene, ticlodipine, timolol, tolazoline, tolazamide, tolmetin, trazodone, triazolam, triethylperazine, trifluopromazine, trihexylphenidyl, trimeprazine, trimipramine, tubocurarine, vecuronium, vidarabine, vinblastine, vincristine, vinorelbine and xylometazoline.

Examples of aromatic heterocyclic amines include, but are not limited to, acetazolamide, acyclovir, adenosine phosphate, allopurinal, alprazolam, amoxapine, amrinone, apraclonidine, azatadine, aztreonam, bisacodyl, bleomycin, brompheniramine, buspirone, butoconazole, carbinoxamine, cefamandole, cefazole, cefixime, cefmetazole, cefonicid, cefoperazone, cefotaxime, cefotetan, cefpodoxime, ceftriaxone, cephapirin, chloroquine, chlorpheniramine, cimetidine, cladarabine, clotrimazole, cloxacillin, didanosine, dipyridamole, doxazosin, doxylamine, econazole, enoxacin, estazolam, ethionamide, famciclovir, famotidine, fluconazole, fludarabine, folic acid, ganciclovir, hydroxychloroquine, iodoquinol, isoniazid, isothipendyl, itraconazole, ketoconazole, lamotrigine, lansoprazole, lorcetadine, losartan, mebendazole, mercaptopurine, methafurylene, methapyriline, methotrexate, metronidazole, miconazole, midazolam, minoxidil, nafzodone, naldixic acid, niacin, nicotine, nifedipine, nizatidine, omeperazole, oxaprozin, oxiconazole, papaverine, pentostatin, phenazopyridine, pheniramine, pilocarpine, piroxicam, prazosin, primaquine, pyrazinamide, pyrilamine, pyrimethamine, pyrithiamine, pyroxidine, quinidine, quinine, ribaverin, rifampin, sulfadiazine, sulfamethizole, sulfamethoxazole, sulfasalazine, sulfasoxazole, terazosin, thiabendazole, thiamine, thioguanine, thonzylamine, timolol, trazodone, triampterene, triazolam, trimethadione, trimethoprim, trimetrexate, triplenamine, tropicamide and vidarabine.

Examples of azo compounds are phenazopyridine and sulfasalazine, while examples of imines include cefixime, cimetidine, clofazimine, clonidine, dantrolene, famotidine, furazolidone, nitrofurantoin, nitrofurazone and oxiconazole.

Combinations of amine drugs and/or combinations of an amine drug with a different type of active agent may also be delivered using the methodology of the present invention.

Formulations

The method of delivery of the pharmacologically active amine may vary, but necessarily involves application of a formulation or drug delivery system containing the amine and a hydroxide-releasing agent to a predetermined area of the skin or other tissue for a period of time sufficient to provide the desired local or systemic effect. The method may involve direct, topical application of the composition as an ointment, gel, cream, or the like, or may involve use of a drug delivery device. In either case, water must be present in order for the hydroxide-releasing agent to generate hydroxide ions and thus enhance the flux of the active agent through the patient's body surface. Thus, a formulation or drug reservoir may be aqueous, i.e., contain water, or may be nonaqueous and used in combination with an occlusive overlayer so that moisture evaporating from the body surface is maintained within the formulation or transdermal system during drug administration. In some cases, however, e.g., with an occlusive gel, a nonaqueous formulation may be used with or without an occlusive layer.

Suitable formulations include ointments, creams, gels, lotions, pastes, and the like. Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: *The Science and Practice of Pharmacy,* 19th Ed. (Easton, Pa.: Mack Publishing Co., 1995), at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, see *Remington: The Science and Practice of Pharmacy* for further information.

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions, as is known in the art, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and can be used as drug delivery systems herein as well. Liposome preparations for use in the instant invention include cationic (positively charged), anionic (negatively charged) and neutral preparations. Cationic liposomes are readily available. For example, N[1-2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. They are generally although not necessarily formed from lipids, preferably charged lipids such as phospholipids. Preparation of lipidic microspheres is well known in the art and described in the pertinent texts and literature.

Various additives, known to those skilled in the art, may be included in the transdermal compositions. For example, solvents, including relatively small amounts of alcohol, may be used to facilitate solubilization of the active agent. Other optional additives include opacifiers, antioxidants, fragrance, colorant, gelling agents, thickening agents, stabilizers, and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

For those drugs having an unusually low rate of permeation through the skin or mucosal tissue, it may be desirable to include a second permeation enhancer in the formulation in addition to the hydroxide-releasing agent, although in a preferred embodiment the hydroxide-releasing agent is administered without any other permeation enhancers. Any other enhancers should, like the hydroxide-releasing agent itself, minimize the possibility of skin damage, irritation, and systemic toxicity. Examples of suitable secondary enhancers (or "co-enhancers") include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450; see also ); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as DMSO and $C_{10}MSO$ may also be used, but are less preferred. As noted earlier herein, *Percutaneous Penetration Enhancers*, eds. Smith et al. (CRC Press, 1995) provides an excellent overview of the field and further information concerning possible secondary enhancers for use in conjunction with the present invention.

The formulation may also contain irritation-mitigating additives to minimize or eliminate the possibility of skin irritation or skin damage resulting from the drug, the enhancer, or other components of the formulation. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the present formulations at a concentration effective to mitigate irritation or skin damage, typically representing not more than about 20 wt. %, more typically not more than about 5 wt. %, of the formulations.

The concentration of the active agent in the formulation can vary a great deal, and will depend on a variety of factors, including the disease or condition to be treated, the desired effect, the ability and speed of the active agent to reach its intended target, and other factors within the particular knowledge of the patient and physician. Preferred formulations will typically contain on the order of about 0.5 wt. % to 50 wt. %, optimally about 10 wt. % to 30 wt. % active agent.

Transdermal Delivery Systems

An alternative and preferred method for administering a pharmacologically active amine transdermally involves the use of a drug delivery system, e.g., a topical or transdermal "patch," wherein the active agent is contained within a laminated structure that is to be affixed to the skin. In such a structure, the drug composition is contained in a layer, or "reservoir," underlying an upper backing layer. The laminated structure may contain a single reservoir, or it may contain multiple reservoirs.

In one embodiment, the reservoir comprises a polymeric matrix of a pharmaceutically acceptable adhesive material that serves to affix the system to the skin during drug delivery; typically, the adhesive material is a pressure-sensitive adhesive (PSA) that is suitable for long-term skin contact, and which should be physically and chemically compatible with the active agent, hydroxide-releasing agent, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene(polychloroprene). Preferred adhesives are polyisobutylenes.

The backing layer functions as the primary structural element of the transdermal system and provides the device with flexibility an, preferably, occlusivity. The material used for the backing layer should be inert and incapable of absorbing drug, hydroxide-releasing agent or components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure includes a release liner. Immediately prior to use, this layer is removed from the device so that the system may be affixed to the skin. The release liner should be made from a drug/vehicle impermeable material, and is a disposable element which serves only to protect the device prior to application. Typically, the release liner is formed from a material impermeable to the pharmacologically active agent and the hydroxide-releasing agent, and which is easily stripped from the transdermal patch prior to use.

In an alternative embodiment, the drug-containing reservoir and skin contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or "pouch," or is may be a hydrogel reservoir, or may take some other form. Hydrogel reservoirs are particularly preferred herein. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly (hydroxyethyl methacrylate) poly(HEMA)), or a copolymer or mixture thereof. Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be a drug, a hydroxide-releasing agent, an additional enhancer, or some other component contained in the drug delivery system.

A rate-controlling membrane, if present, will be included in the system on the skin side of one or more of the drug reservoirs. The materials used to form such a membrane are selected to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device, i.e., the skin contact area, has an area in the range of about 5 $cm^2$ to 200 $cm^2$, preferably 5 $cm^2$ to 100 $cm^2$, more preferably 20 $cm^2$ to 60 $cm^2$. That area will vary, of course, with the amount of the drug to be delivered and the flux of the drug through the body surface. Larger patches will be necessary to accomodate larger quantities of drug, while smaller patches can be used for small quantities of drug and/or drugs that exhibit a relatively high permeation rate.

Such drug delivery systems may be fabricated using conventional coating and laminating techniques known in the art. For example adhesive matrix systems can be prepared by casting a fluid admixture adhesive, drug and vehicle onto the backing layer followed by lamination of the release liner. Similarly the adhesive mixture may be cast onto the release liner, followed by lamination of the release liner. Alternatively, the drug reservoir may be prepared in the absence of drug or excipient, and then loaded by "soaking" in a drug/vehicle mixture. In general, transdermal systems of the invention are fabricated by solvent evaporation, film casting, melt extrusion, thin film lamination, die cutting, or the like. The hydroxide-releasing agent will generally be incorporated into the device during patch manufacture rather than subsequent to preparation of the device. For active agents that are obtained in salt form, an enhancer that doubles as a neutralizing agent is incorporated into the device during patch manufacture rather than subsequent to preparation of the device. Thus, for acid addition salts of an amine drug, e.g., the hydrochloride salt of racemic phenylpropanolamine, a basic enhancer such as a hydroxide-releasing agent will neutralize the drug during manufacture of the transdermal system, resulting in a final drug delivery device in which the drug is present in nonionized, neutral form, preferably along with an excess of the basic compound to serve as a permeation enhancer.

Other types and configurations of transdermal drug delivery systems may also be used in conjunction with the method of the present invention, i.e., the use of a hydroxide-releasing agent as a permeation enhancer for a pharmacologically active amine, as will be appreciated by those skilled in the art of transdermal drug delivery. See, for example, Ghosh, *Transdermal and Topical Drug Delivery Systems* (Interpharm Press, 1997), particularly Chapters 2 and 8.

As with the formulations of the invention discussed in the preceding section, the composition containing the pharmacologically active amine within the drug reservoir(s) of these laminated system may contain a number of components. In some cases, the drug and hydroxide-releasing agent may be delivered "neat," i.e., in the absence of additional liquid. In most cases, however, the drug will be dissolved, dispersed or suspended in a suitable pharmaceutically acceptable vehicle, typically a solvent or gel. Other components which may be present include preservatives, stabilizers, surfactants, and the like.

The invention accordingly provides a novel and highly effective means for administering a pharmacologically active amine through the body surface (skin or mucosal tissue) of a human or animal. Surprisingly, the increase in permeation achieved by co-administration of a basic enhancer is not accompanied by any noticeable tissue damage, irritation, or sensitization. The invention thus represents an important advance in the field of transdermal drug delivery.

The practice of the present invention will employ, unless otherwise indicated, conventional techniques of drug formulation, particularly topical drug formulation, which are within the skill of the art. Such techniques are fully explained in the literature. See Remington: The Science and Practice of Pharmacy, cited supra, as well as Goodman & Gilman's The Pharmacological Basis of Therapeutics, 9th Ed. (New York: McGraw-Hill, 1996).

It is to be understood that while the invention has been described in conjunction with the preferred specific embodiments thereof, the foregoing description, as well as the examples which follow, are intended to illustrate and not limit the scope of the invention. Other aspects, advantages and modifications will be apparent to those skilled in the art to which the invention pertains. All patents, patent applications, journal articles and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

EXAMPLE 1

An in vitro skin permeation study was conducted using four phenylpropanolamine hydrochloride (PPA-HCl) transdermal systems. The formulations used to prepare these systems are listed in Table 1, which includes weight and weight percent of each component in the formulations. The weight of sodium hydroxide was 0 g, 0.165 g, 0.195 g, and 0.23 g for formulation #PPA-N7, -N1, -N2, -and -N5, respectively. Each formulation was coated onto a release liner and dried in an oven at 55° C. for two hours to remove water and other solvents. The dried drug-in-adhesive/release liner film was laminated to a backing film. The backing/drug-in-adhesive/release liner laminate was then cut into round discs with a diameter of $^{11}/_{16}$ inch. The theoretical percent weight for each component after drying (calculated assuming all the volatile ingredients were completely removed during drying) is listed in Table 2.

The in vitro permeation of PPA-HCl through human cadaver skin from these discs was performed using Franz-type diffusion cells with a diffusion area of 1 $cm^2$. The volume of receiver solution was 8 ml. Human cadaver skin was cut to the desired size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

The cells were filled with DI water. The receiver solution was completely withdrawn and replaced with fresh DI water at each time point. The samples taken were analyzed by an HPLC for the concentration of PPA-HCl in the receiver solution. The cumulative amount of PPA-HCl that permeated across the human cadaver skin was calculated using the measured PPA-HCl concentrations in the receiver solutions, which were plotted versus time and shown in FIG. 1.

Since PPA-HCl is an acid addition salt of a free base, it reacts with NaOH. The concentration of NaOH in the system after the reaction is completed depends on the amount of PPA-HCl added. The remaining NaOH concentration after the reaction is completed is defined as "excess NaOH concentration," calculated as explained in the foregoing example. The excess NaOH concentration for four PPA-HCl systems, #PPA-N7, -N1, -N2, -and -N5, were calculated and listed in Table 3.

The pH of the patch was measured using the following procedures. A 2.5 $cm^2$ circular patch was punched out. Ten ml purified water was pipetted into a glass vial, and a stir bar was added; the liner was removed from the patch and placed in the vial along with the patch. The vial was then placed on a stir plate and the water/patch/liner mixture was stirred for 5 minutes, at which point the liner was removed from the vial and discarded. The vial was again placed on a stir plate and stirring continued for an additional 18 hours. After 18 hours, the stir bar was removed from the vial and the pH of the solution determined using a calibrated pH meter. The measured pHs for the PPA-HCl transdermal systems are listed in Table 3.

TABLE 1

Weight and Weight Percent of Each Component (Based on Total Solution Weight) for Four PPA-HCl Transdermal Systems

|  | PPA-N7 | PPA-N1 | PPA-N2 | PPA-N5 |
| --- | --- | --- | --- | --- |
| PPA-HCl | 0.75 g (8.5%) | 0.75 g (8.2%) | 0.75 g (8.1%) | 0.75 g (8.1%) |
| NaOH | 0 | 0.165 g (1.8%) | 0.195 g (2.1%) | 0.23 g (2.5%) |
| DI water | 1.1 g (12.4%) | 1.265 g (13.8%) | 1.295 g (14.0%) | 1.33 g (14.3%) |
| Propylene glycol | 0.5 g (5.6%) | 0.5 g (5.4%) | 0.5 g (5.4%) | 0.5 g (5.4%) |
| Methylal | 1 g (11.3%) | 1 g (10.9%) | 1 g (10.8%) | 1 g (10.7%) |
| Heptane | 1.5 g (16.9%) | 1.5 g (16.3%) | 1.5 g (16.2%) | 1.5 g (16.1%) |
| PIB adhesive (30% solid) | 4 g (45.2%) | 4 g (43.6%) | 4 g (43.3%) | 4 g (43.0%) |

TABLE 2

Weight and Theoretical Weight Percent of Each Component in the Dried Film for Four PPA-HCl Transdermal Systems

|  | PPA-N7 | PPA-N1 | PPA-N2 | PPA-N5 |
| --- | --- | --- | --- | --- |
| PPA-HCl | 0.75 g (30.6%) | 0.75 g (28.7%) | 0.75 g (28.4%) | 0.75 g (28.0%) |
| NaOH | 0 | 0.165 g (6.3%) | 0.195 g (7.4%) | 0.23 g (8.6%) |
| PIB adhesive | 1.2 g (49.0%) | 1.2 g (45.9%) | 1.2 g (45.4%) | 1.2 g (44.8%) |
| Propylene glycol | 0.5 g (20.4%) | 0.5 g (19.1%) | 0.5 g (18.9%) | 0.5 g (18.7%) |

TABLE 3

Excess NaOH Concentration and pH of Four PPA-HCl Transdermal Systems

|  | PPA-N7 | PPA-N1 | PPA-N2 | PPA-N5 |
| --- | --- | --- | --- | --- |
| Excess NaOH Concentration (wt. %) |  | 0.20% | 1.33% | 2.62% |
| pH | 7.33 | 10.08 | 10.16 | 10.88 |

Even though patch #PPA-N1 contained 6.3% NaOH (Table 2), the cumulative amount of PPA-HCl that permeated across the human cadaver skin at 24 hours from this formulation (1.35 mg/cm$^2$, FIG. 1) was only slightly higher than that from the formulation without NaOH (PPA-N7, 0.56 mg/cm$^2$). This may be due to the consumption of NaOH by the reaction between NaOH and PPA-HCl, which reduced the NaOH concentration to only 0.20% as the excess NaOH concentration shown in Table 3. This result indicated that the permeation of PPA-HCl could be enhanced with an excess NaOH concentration as low as 0.20%.

The cumulative amount of PPA-HCl across human cadaver skin at 24 hours increased from 1.35 mg/cm$^2$ to 5.99 mg/cm$^2$ when the calculated excess NaOH concentration in the dried patch was increased from 0.20% to 2.62%. The cumulative amount of PPA-HCl across human cadaver skin at 24 hours from the formulation with an excess NaOH concentration of 1.33% (PPA-N2, 5.2 mg/cm$^2$) is about 5 times higher than that from the formulation with an excess NaOH concentration of 0.20% (PPA-N1, 1.35 mg/cm$^2$).

The pH of the PPA-HCl patch increased from 10.08 to 10.88 when the calculated excess NaOH concentration in the dried patch was increased from 0.20% to 2.62%. Skin irritation could be related to the pH of the patch, which depends on the excess NaOH concentration.

EXAMPLE 2

Figure 2:
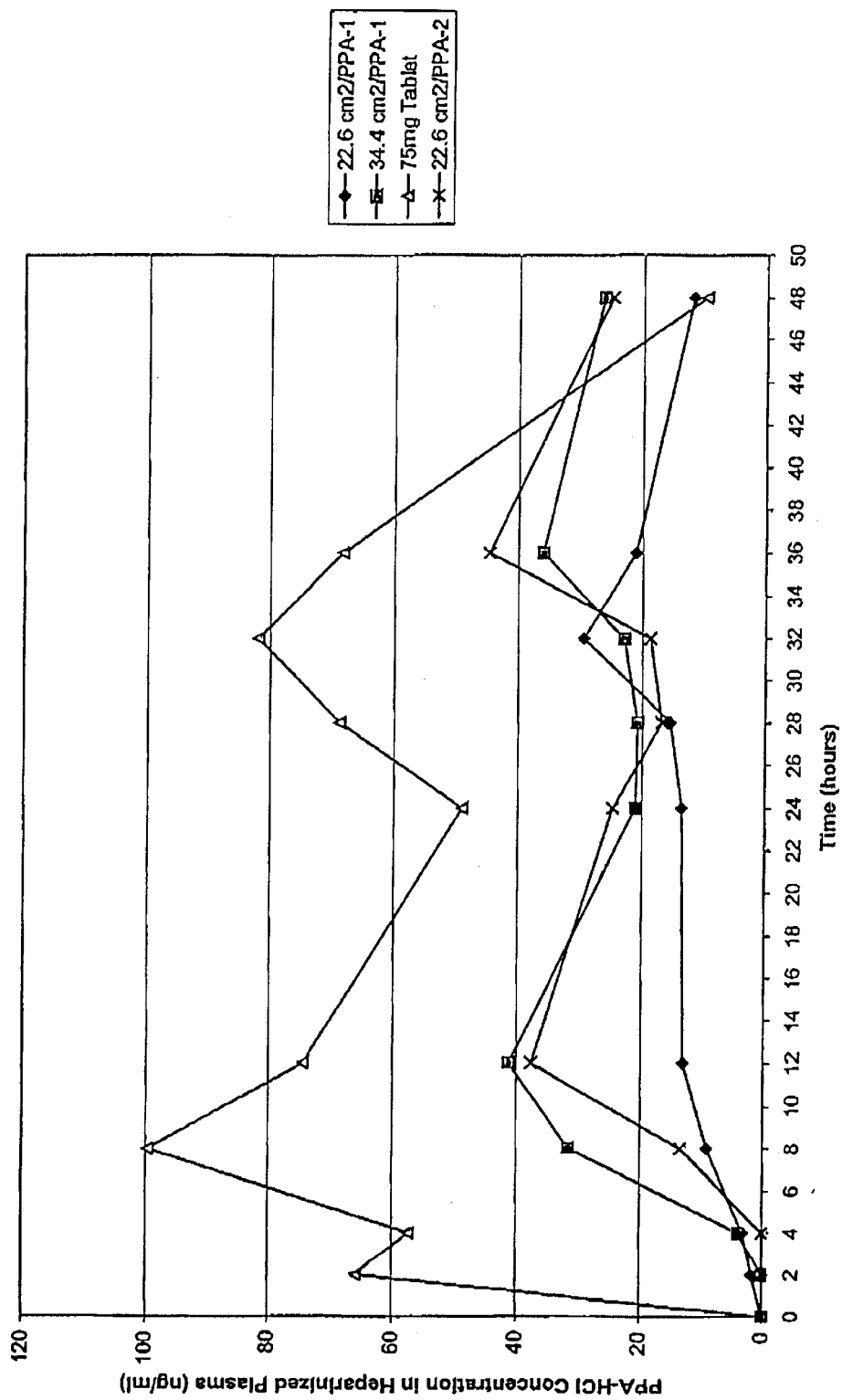
FIG. 2 is a graph illustrating the cumulative amount of racemic phenylpropanolamine permeated from matrix patches as described in Example 2.

An in vitro skin permeation study was conducted using four phenylpropanolamine hydrochloride (PPA-HCl) transdermal systems. The formulations used to prepare these systems are listed in Table 4, which includes weight and weight percent of each component in the formulations. The weight of sodium carbonate (Na$_2$CO$_3$) was 0 g, 0.29 g, 0.44 g, and 0.74 g for formulations #PPA-PC1, -PC2, -PC3, and -PC4 respectively. The matrix patches were prepared and evaluated using the same procedures as set forth in Example 1. The theoretical percent weight for each ingredient after drying (calculated assuming all the volatile ingredients were completely removed during drying) is listed in Table 5. The cumulative amount of PPA-HCl across human cadaver skin was calculated using the measured PPA-HCl concentrations in the receiver solutions, which are shown in Table 6 and FIG. 2.

Since PPA-HCl is a salt of a free base, it reacts with Na$_2$CO$_3$. The concentration of Na$_2$CO$_3$ in the system after the reaction is completed depends on the amount of PPA-HCl added. The remaining sodium carbonate concentration after the reaction is completed is defined as "excess Na$_2$CO$_3$ concentration," which is calculated by the following equation.

$$[Na_2CO_3\ _{excess}]=[Na_2CO_3\ _{total}]-[Na_2CO_3\ _{needed\ for\ neutralization}]$$

The excess Na$_2$CO$_3$ concentration for four PPA-HCl systems, #PPA-PC1, -PC2, -PC3 and -PC4 were calculated and listed in Table 7.

The pH of the patch was determined using the procedure of example 1 and the results are listed in Table 7.

TABLE 4

Weight and Weight Percent of Each Component (Based on Total Solution Weight) for Four PPA-HCl Transdermal Systems

|  | PPA-PC1 | PPA-PC2 | PPA-PC3 | PPA-PC4 |
| --- | --- | --- | --- | --- |
| PPA-HCl | 0.5 g (6.7%) | 0.5 g (5.7%) | 0.5 g (5.6%) | 0.5 g (5.5%) |
| Na$_2$CO$_3$ | 0 | 0.29 g (3.3%) | 0.44 g (5.0%) | 0.74 g (8.1%) |
| DI water | 1.0 g (13.5%) | 2.0 g (23.0%) | 2.0 g (22.6%) | 2.0 g (21.9%) |
| Methyl alcohol | 0.5 g (6.7%) | 0.5 g (5.7%) | 0.5 g (5.6%) | 0.5 g (5.5%) |
| Propylene glycol | 0.2 g (2.7%) | 0.2 g (2.3%) | 0.2 g (2.3%) | 0.2 g (2.2%) |
| HPMC | 0.01 g (0.1%) | 0.01 g (0.1%) | 0.01 g (0.1%) | 0.01 g (0.1%) |
| Heptane | 1.2 g (16.2%) | 1.2 g (13.8%) | 1.2 g (13.6%) | 1.2 g (13.1%) |
| PIB adhesive (30% solid) | 4 g (54.0%) | 4 g (46.0%) | 4 g (45.2%) | 4 g (45.2%) |

TABLE 5

Weight and Theoretical Weight Percent of Each Component in the Dried Film for Four PPA-HCl Transdermal Systems

|  | PPA-PC1 | PPA-PC2 | PPA-PC3 | PPA-PC4 |
| --- | --- | --- | --- | --- |
| PPA-HCl | 0.5 g (26.2%) | 0.5 g (22.7%) | 0.5 g (21.3%) | 0.5 g (18.9%) |
| $Na_2CO_3$ | 0 | 0.29 g (13.2%) | 0.44 g (18.7%) | 0.74 g (27.9%) |
| Propylene glycol | 0.2 g (10.5%) | 0.2 g (9.1%) | 0.2 g (8.5%) | 0.2 g (7.5%) |
| HPMC | 0.01 g (0.5%) | 0.01 g (0.5%) | 0.01 g (0.4%) | 0.01 g (0.4%) |
| PIB adhesive | 1.2 g (62.8%) | 1.2 g (54.5%) | 1.2 g (51.1%) | 1.2 g (45.3%) |

TABLE 6

Cumulative Amount of PPA-HCl across human cadaver skin for PPA-HCl Transdermal Systems ($\mu g/cm^2$)

|  | PPA-PC1 | PPA-PC2 | PPA-PC3 | PPA-PC4 |
| --- | --- | --- | --- | --- |
| 5 hours | 152.8 | 68.0 | 81.1 | 144.8 |
| 15 hours | 359.5 | 222.7 | 400.8 | 631.2 |
| 19 hours | 442.7 | 295.7 | 551.5 | 864.3 |
| 24 hours | 545.1 | 410.4 | 705.6 | 1147.5 |

TABLE 7

Excess $Na_2CO_3$ Concentration and pH of Four PPA-HCl Transdermal Systems

|  | PPA-PC1 | PPA-PC2 | PPA-PC3 | PPA-PC4 |
| --- | --- | --- | --- | --- |
| Excess $Na_2CO_3$ Concentration (wt. %) | — | 0.4% | 6.7% | 16.7% |
| pH | 6.54 | 9.81 | 9.86 | 10.17 |

Even though patch #PPA-PC2 contained 13.2% $Na_2CO_3$ (Table 5), the cumulative amount of PPA-HCl that permeated across the human cadaver skin at 24 hours (410.4 $\mu g/cm^2$, Table 6) was lower than that from the formulation without $Na_2CO_3$ (PPA-PC1, 545.1 $\mu g/cm^2$). This may be due to the consumption of $Na_2CO_3$ by the reaction between $Na_2CO_3$ and PPA-HCl, which reduced the $Na_2CO_3$ concentration to only 0.4% as the excess $Na_2CO_3$ concentration (Table 7).

When the calculated excess $Na_2CO_3$ concentration in the dried patch was further increased from 0.4% to 16.7%, the cumulative amount of PPA-HCl that permeated across the human cadaver skin at 24 hours was increased from 410.4 to 1147.5 $\mu g/cm^2$. This result indicated that the permeation of PPA-HCl could be enhanced by $Na_2CO_3$, even though the required excess $Na_2CO_3$ concentration is higher than that of NaOH. Greater amounts of $Na_2CO_3$ may be necessary because it is a weaker base compared to NaOH and the molecular weight of $Na_2CO_3$ is higher than that of NaOH.

The pH of the PPA-HCl patch measured using the procedures listed above increased from 9.81 to 10.17 when the calculated excess $Na_2CO_3$ concentration in the dried patch was increased from 0.4% to 16.7%.

EXAMPLE 3

An in vitro skin permeation study was conducted using four phenylpropanolamine hydrochloride (PPA-HCl) transdermal systems. The formulations used to prepare these systems are listed in Table 8, which includes weight and weight percent of each component in the formulations. The weight of potassium phosphate, tribasic ($K_3PO_4$) was 0 g, 0.57 g, 0.6 g, and 0.66 g for formulation #PPA-PK1, -PK2, -PK3, and -PK4 respectively. The matrix patches were prepared and evaluated using the same procedures as set forth in Example 1. The theoretical percent weight for each ingredient after drying (calculated assuming all the volatile ingredients were completely removed during drying) is listed in Table 9. The cumulative amount of PPA-HCl across human cadaver skin was calculated using the measured PPA-HCl concentrations in the receiver solutions, which were shown in Table 10 and FIG. 3.

Since PPA-HCl is a salt of a free base, it reacts with $K_3PO_4$. The concentration of $K_3PO_4$ in the system after the reaction is completed depends on the amount of PPA-HCl added. The remaining $K_3PO_4$ concentration after the reaction is completed is defined as "excess $K_3PO_4$ concentration," which is calculated by the following equation.

$$[K_3PO_{4\ excess}] = [K_3PO_{4\ total}] - [K_3PO_{4\ needed\ for\ neutralization}]$$

The excess $K_3PO_4$ concentration for four PPA-HCl systems, #PPA-PK1, -PK2, -PK3 and -PK4 were calculated and listed in Table 11.

The pH of the patch was determined using the procedure of Example 1 and the results are listed in Table 11.

TABLE 8

Weight and Weight Percent of Each Component (Based on Total Solution Weight) for Four PPA-HCl Transdermal Systems

|  | PPA-PK1 | PPA-PK2 | PPA-PK3 | PPA-PK4 |
| --- | --- | --- | --- | --- |
| PPA-HCl | 0.5 g (6.6%) | 0.5 g (6.1%) | 0.5 g (6.1%) | 0.5 g (6.1%) |
| $K_3PO_4$ | 0 | 0.57 g (7.0%) | 0.6 g (7.3%) | 0.66 g (8.0%) |
| DI water | 1.0 g (13.2%) | 1.0 g (12.2%) | 1.0 g (12.2%) | 1.0 g (12.1%) |
| Propylene glycol | 0.5 g (6.6%) | 0.5 g (6.1%) | 0.5 g (6.1%) | 0.5 g (6.1%) |
| Methyl alcohol | 0.5 g (6.6%) | 0.5 g (6.1%) | 0.5 g (6.1%) | 0.5 g (6.1%) |
| PIB adhesive (30% solid) | 4 g (52.6%) | 4 g (49.0%) | 4 g (48.8%) | 4 g (48.4%) |

TABLE 8-continued

Weight and Weight Percent of Each Component (Based on Total Solution Weight) for Four PPA-HCl Transdermal Systems

|  | PPA-PK1 | PPA-PK2 | PPA-PK3 | PPA-PK4 |
|---|---|---|---|---|
| HPMC | 0.1 g (1.3%) | 0.1 g (1.2%) | 0.1 g (1.2%) | 0.1 g (1.2%) |
| Heptane | 1 g (13.2%) | 1 g (12.2%) | 1 g (12.2%) | 1 g (12.1%) |

TABLE 9

Weight and Theoretical Weight Percent of Each Component in the Dried Film for Four PPA-HCl Transdermal Systems

|  | PPA-PK1 | PPA-PK2 | PPA-PK3 | PPA-PK4 |
|---|---|---|---|---|
| PPA-HCl | 0.5 g (21.7%) | 0.5 g (17.4%) | 0.5 g (17.2%) | 0.5 g (16.9%) |
| $K_3PO_4$ | 0 | 0.57 g (19.9%) | 0.6 g (20.7%) | 0.66 g (22.3%) |
| Propylene glycol | 0.5 g (21.7%) | 0.5 g (17.4%) | 0.5 g (17.2%) | 0.5 g (16.9%) |
| PIB adhesive | 1.2 g (52.2%) | 1.2 g (41.8%) | 1.2 g (41.4%) | 1.2 g (40.5%) |
| HPMC | 0.1 g (4.3%) | 0.1 g (3.5%) | 0.1 g (3.4%) | 0.1 g (3.4%) |

TABLE 10

Cumulative Amount of PPA-HCl across human cadaver skin for PPA-HCl Transdermal Systems ($\mu g/cm^2$)

|  | PPA-PK1 | PPA-PK2 | PPA-PK3 | PPA-PK4 |
|---|---|---|---|---|
| 5 hours | 94.7 | 660.0 | 421.6 | 362.9 |
| 16 hours | 445.9 | 1701.3 | 1420.3 | 1607.5 |
| 20 hours | 576.8 | 1919.2 | 1633.1 | 1872.5 |
| 24 hours | 680.5 | 2055.2 | 1762.9 | 2021.1 |

TABLE 11

Excess $K_3PO_4$ Concentration and pH of Four PPA-HCl Transdermal Systems

|  | PPA-PK1 | PPA-PK2 | PPA-PK3 | PPA-PK4 |
|---|---|---|---|---|
| Excess $K_3PO_4$ Concentration (wt. %) | — | 0.2% | 1.2% | 3.2% |
| pH | 6.75 | 9.68 | 9.62 | 10.08 |

The cumulative amount of PPA-HCl that permeated across the human cadaver skin at 24 hours for PPA-PK2 (2055.2 $\mu g/cm^2$, Table 10) with a calculated excess $K_3PO_4$ concentration of 0.2% was three times higher than that from the formulation without $K_3PO4$ (PPA-PK1, 680.5 $\mu g/cm^2$). This result indicated that the permeation of PPA-HCl could be enhanced with an excess $K_3PO_4$ concentration as low as 0.2%.

The cumulative amount of PPA-HCl across human cadaver skin at 24 hours remained about the same when the excess $K_3PO_4$ concentration in the dried patch was increased from 0.2% to 3.2% (Tables 10 and 11).

The pH of the PPA-HCl patch measured using the procedures listed above increased from 6.75 to 9.68 when the $K_3PO_4$ concentration in the dried patch was increased from 0% to 19.9% (or 0.2% excess $K_3PO_4$ concentration, Tables 9 and 11). However, the pH of the PPA-HCl patch remained about the same when the excess $K_3PO_4$ concentration in the dried patch was further increased from 0.2% to 3.2% (Table 11).

EXAMPLE 4

An in vitro skin permeation study was conducted using four phenylpropanolamine hydrochloride (PPA-HCl) transdermal systems. The formulations used to prepare these systems are listed in Table 12, which includes weight and weight percent of each component in the formulations. The weight of potassium phosphate, tribasic ($K_3PO_4$) was 0 g, 0.57 g, 0.73 g, and 1.05 g for formulation #PPA-PK1R, -PK2R, -PK5, and -PK6 respectively. The matrix patches were prepared and evaluated using the same procedures as set forth in Example 1. The theoretical percent weight for each ingredient after drying (calculated assuming all the volatile ingredients were completely removed during drying) is listed in Table 13. The cumulative amount of PPA-HCl across human cadaver skin was calculated using the measured PPA-HCl concentrations in the receiver solutions, which were shown in Table 14 and FIG. 4.

The excess $K_3PO_4$ concentration for four PPA-HCl systems, #PPA-PK1R, -PK2R, -PK5 and -PK6 were calculated using the procedure of Example 3 and the results are listed in Table 15. The pH of each patch was determined using the procedure of Example 1 and the results are listed in Table 15.

TABLE 12

Weight and Weight Percent of Each Component (Based on Total Solution Weight) for Four PPA-HCl Transdermal Systems

|  | PPA-PK1R | PPA-PK2R | PPA-PK5 | PPA-PK6 |
|---|---|---|---|---|
| PPA-HCl | 0.5 g (6.9%) | 0.5 g (6.4%) | 0.5 g (6.3%) | 0.5 g (6.1%) |
| $K_3PO_4$ | 0 | 0.57 g (7.3%) | 0.73 g (9.2%) | 1.05 g (12.7%) |
| DI water | 1.0 g (13.9%) | 1.0 g (12.9%) | 1.0 g (12.6%) | 1.0 g (12.1%) |
| Methyl alcohol | 0.5 g (6.9%) | 0.5 g (6.4%) | 0.5 g (6.3%) | 0.5 g (6.1%) |

TABLE 12-continued

Weight and Weight Percent of Each Component (Based on Total Solution Weight) for Four PPA-HCl Transdermal Systems

|  | PPA-PK1R | PPA-PK2R | PPA-PK5 | PPA-PK6 |
|---|---|---|---|---|
| Propylene glycol | 0.2 g (2.8%) | 0.2 g (2.6%) | 0.2 g (2.5%) | 0.2 g (2.4%) |
| HPMC | 0.01 g (0.1%) | 0.01 g (0.1%) | 0.01 g (0.1%) | 0.01 g (0.1%) |
| Heptane | 1 g (13.9%) | 1 g (12.9%) | 1 g (12.6%) | 1 g (12.1%) |
| PIB adhesive (30% solid) | 4 g (55.5%) | 4 g (51.4%) | 4 g (50.4%) | 4 g (48.4%) |

TABLE 13

Weight and Theoretical Weight Percent of Each Component in the Dried Film for Four PPA-HCl Transdermal Systems

|  | PPA-PK1R | PPA-PK2R | PPA-PK5 | PPA-PK6 |
|---|---|---|---|---|
| PPA-HCl | 0.5 g (26.2%) | 0.5 g (20.2%) | 0.5 g (18.9%) | 0.5 g (16.5%) |
| $K_3PO_4$ | 0 | 0.57 g (23.6%) | 0.73 g (27.7%) | 1.05 g (35.5%) |
| Propylene glycol | 0.2 g (10.5%) | 0.2 g (8.1%) | 0.2 g (7.6%) | 0.2 g (6.8%) |
| HPMC | 0.01 g (0.5%) | 0.01 g (0.4%) | 0.01 g (0.4%) | 0.01 g (0.3%) |
| PIB adhesive | 1.2 g (62.8%) | 1.2 g (48.4%) | 1.2 g (45.5%) | 1.2 g (40.5%) |

TABLE 14

Cumulative Amount of PPA-HCl across human cadaver skin for PPA-HCl Transdermal Systems ($\mu g/cm^2$)

|  | PPA-PK1R | PPA-PK2R | PPA-PK5 | PPA-PK6 |
|---|---|---|---|---|
| 5 hours | 336.8 | 553.1 | 291.5 | 186.7 |
| 16 hours | 879.5 | 1702.4 | 1172.5 | 873.1 |
| 20 hours | 1091.2 | 2031.2 | 1711.5 | 1204.3 |
| 24 hours | 1324.0 | 2378.4 | 2222.7 | 1628.0 |

TABLE 15

Excess $K_3PO_4$ Concentration and pH of Four PPA-HCl Transdermal Systems

|  | PPA-PK1R | PPA-PK2R | PPA-PK5 | PPA-PK6 |
|---|---|---|---|---|
| Excess $K_3PO_4$ Concentration (wt. %) |  | 0.2% | 6.2% | 16.4% |
| pH | 7 | 9.72 | 10.17 | 10.44 |

The cumulative amount of PPA-HCl that permeated across the human cadaver skin at 24 hours for PPA-PK2R (2378.4 $\mu g/cm^2$, Table 14) with a calculated excess $K_3PO4$ concentration of 0.2% was about two times higher than that from the formulation without $K_3PO_4$ (PPA-PK1R, 1324.0 $\mu g/cm^2$). This result indicated that the permeation of PPA-HCl is enhanced with an excess $K_3PO_4$ concentration as low as 0.2%.

The cumulative amount of PPA-HCl across human cadaver skin at 24 hours remained about the same when the excess $K_3PO_4$ concentration in the dried patch was increased from 0.2% to 6.2% (Tables 14 and 15). When the excess $K_3PO_4$ concentration in the dried patch was further increased from 6.2% to 16.4% (Table 15), the cumulative amount of PPA-HCl across human cadaver skin at 24 hours decreased from 2222.7 to 1628.0 $\mu g/cm^2$. This decrease in flux may be because the high concentration of $K_3PO_4$ made the adhesive matrix more hydrophobic and the amount of $K_3PO_4$ that could be dissolved by the small amount of water on the top of the skin was reduced.

The pH of the PPA-HCl patch measured using the procedures listed above increased from 7 to 9.72 when the $K_3PO_4$ concentration in the dried patch was increased from 0% to 23% (or 0.2% excess $K_3PO_4$ concentration, Tables 13 and 15). The pH of the PPA-HCl patch increased from 9.72 to 10.44 when the excess $K_3PO_4$ concentration in the dried patch was further increased from 0.2% to 16.4% (Table 15).

EXAMPLE 5

An in vitro skin permeation study was conducted using four phenylpropanolamine hydrochloride (PPA-HCl) transdermal systems. The formulations used to prepare these systems are listed in Table 16, which includes weight and weight percent of each component in the formulations. The weight of magnesium oxide (MgO) was 0 g, 0.11 g, 0.26 g and 0.50 g for formulation #PPA-PM1, -PM2, -PM3, and -PM4 respectively. The matrix patches were prepared and evaluated using the same procedures as set forth in Example 1. The theoretical percent weight for each ingredient after drying (calculated assuming all the volatile ingredients were completely removed during drying) is listed in Table 17. The cumulative amount of PPA-HCl across human cadaver skin was calculated using the measured PPA-HCl concentrations in the receiver solutions, which were shown in Table 18 and FIG. 5.

Since PPA-HCl is a salt of a free base, it reacts with MgO. The concentration of MgO in the system after the reaction is completed depends on the amount of PPA-HCl added. The remaining MgO concentration after the reaction is completed is defined as "excess MgO concentration," which is calculated by the following equation.

$$[MgO_{excess}] = [MgO_{total}] - [MgO_{needed\ for\ neutralization}]$$

The excess MgO concentration for four PPA-HCl systems, #PPA-PM1, -PM2, -PM3 and -PM4 were calculated and listed in Table 19.

The pH of the patch was determined using the procedure of Example 1 and the results are listed in Table 19.

TABLE 16

Weight and Weight Percent of Each Component (Based on Total Solution Weight) for Four PPA-HCl Transdermal Systems

|  | PPA-PM1 | PPA-PM2 | PPA-PM3 | PPA-PM4 |
| --- | --- | --- | --- | --- |
| PPA-HCl | 0.5 g (6.9%) | 0.5 g (6.0%) | 0.5 g (5.9%) | 0.5 g (5.7%) |
| MgO | 0 | 0.11 g (1.3%) | 0.26 g (3.1%) | 0.50 g (5.7%) |
| DI water | 1.0 g (13.9%) | 2.0 g (24.0%) | 2.0 g (23.6%) | 2.0 g (22.9%) |
| Methyl alcohol | 0.5 g (6.9%) | 0.5 g (6.0%) | 0.5 g (5.9%) | 0.5 g (5.7%) |
| Propylene glycol | 0.2 g (2.8%) | 0.2 g (2.4%) | 0.2 g (2.4%) | 0.2 g (2.3%) |
| HPMC | 0.02 g (0.3%) | 0.02 g (0.2%) | 0.02 g (0.2%) | 0.02 g (0.2%) |
| PIB adhesive (30% solid) | 4 g (55.4%) | 4 g (48.0%) | 4 g (47.2%) | 4 g (45.9%) |
| Heptane | 1.0 g (13.9%) | 1.0 g (12.0%) | 1.0 g (11.8%) | 1.0 g (11.5%) |

TABLE 17

Weight and Theoretical Weight Percent of Each Component in the Dried Film for Four PPA-HCl Transdermal Systems

|  | PPA-PM1 | PPA-PM2 | PPA-PM3 | PPA-PM4 |
| --- | --- | --- | --- | --- |
| PPA-HCl | 0.5 g (26.0%) | 0.5 g (24.6%) | 0.5 g (22.9%) | 0.5 g (20.7%) |
| MgO | 0 | 0.11 g (5.4%) | 0.26 g (11.9%) | 0.50 g (20.7%) |
| Propylene glycol | 0.2 g (10.4%) | 0.2 g (9.9%) | 0.2 g (9.2%) | 0.2 g (8.3%) |
| HPMC | 0.02 g (1.0%) | 0.02 g (1.0%) | 0.02 g (0.9%) | 0.02 g (0.8%) |
| PIB adhesive | 1.2 g (62.5%) | 1.2 g (59.1%) | 1.2 g (55.0%) | 1.2 g (49.6%) |

TABLE 18

Cumulative Amount of PPA-HCl Across Human Cadaver Skin for PPA-HCl Transdermal Systems ($\mu g/cm^2$)

|  | PPA-PM1 | PPA-PM2 | PPA-PM3 | PPA-PM4 |
| --- | --- | --- | --- | --- |
| 5 hours | 18.7 | 296.8 | 222.1 | 489.4 |
| 15 hours | 77.8 | 621.5 | 1362.9 | 1255.2 |
| 19 hours | 102.7 | 711.4 | 1920.9 | 1524.9 |
| 24 hours | 129.8 | 801.9 | 2533.4 | 1831.3 |

TABLE 19

Excess MgO Concentration and pH of Four PPA-HCl Transdermal Systems

|  | PPA-PM1 | PPA-PM2 | PPA-PM3 | PPA-PM4 |
| --- | --- | --- | --- | --- |
| Excess MgO Concentration (wt. %) |  | 0.1% | 7.0% | 16.2% |
| pH | 7.89 | 9.60 | 10.09 | 10.10 |

The cumulative amount of PPA-HCl that permeated across the human cadaver skin at 24 hours for PPA-PM2 (801.9 $\mu g/cm^2$, Table 18) with a calculated excess MgO concentration of 0.1% was about six times higher than that from the formulation without MgO (PPA-PM1, 129.8 $\mu g/cm^2$). This result indicated that the permeation of PPA-HCl is enhanced with an excess MgO concentration as low as 0.1%.

The cumulative amount of PPA-HCl across human cadaver skin at 24 hours increased from 801.9 to 2533.4 $\mu g/cm^2$ when the excess MgO concentration in the dried patch was increased from 0.1% to 7.0% (Tables 18 and 19). When the excess MgO concentration in the dried patch was further increased from 7.0% to 16.2% (Table 19), the cumulative amount of PPA-HCl across human cadaver skin at 24 hours decreased from 2533.4 to 1831.3 $\mu g/cm^2$. This decrease in flux may be because the high concentration of MgO made the adhesive matrix more hydrophobic and the amount of MgO that could be dissolved by the small amount of water on the top of the skin was reduced.

The pH of the PPA-HCl patch measured using the procedures listed above increased from 7.89 to 9.60 when the MgO concentration in the dried patch was increased from 0% to 5.4% (or 0.1% excess MgO concentration, Tables 17 and 19). The pH of the PPA-HCl remained about the same when the excess MgO concentration in the dried patch was further increased from 0.1% to 16.2% (Table 19).

EXAMPLE 6

An in-vitro skin permeation study was conducted using three oxybutynin HCl transdermal systems. The formulations used to prepare these systems are listed in Table 20, which include weight and weight percent of each ingredient in the formulations. The weight of sodium hydroxide (NaOH) was 0.15 g, 0.25 g, and 0.35 g for formulation #Oxy-P1, -P2, and -P3 respectively. Each formulation was coated on a release liner and dried in an oven at 55° C. for two hours to remove water and other solvents. The dried drug-in-adhesive/release liner film was laminated to a backing film. The backing/drug-in-adhesive/release liner laminate was then cut into round discs with a diameter of 11/16 inch. The theoretical percent weight for each ingredient after drying (calculated assuming all the volatile ingredients were completely removed during drying) is listed in Table 21.

The in-vitro permeation of oxybutynin HCl through human cadaver skin from these discs was performed using Franz-type diffusion cells with a diffusion area of 1 $cm^2$. The volume of receiver solution was 8 ml. Human cadaver skin was cut to desired size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

The cells were filled with 10% ethanol/90% water solution. The receiver solution was completely withdrawn and replaced with fresh ethanol/water solution at each time point. The samples taken were analyzed by an HPLC for the concentration of oxybutynin HCl in the receiver solution. The cumulative amount of oxybutynin HCl across human cadaver skin was calculated using the measured oxybutynin HCl concentrations in the receiver solutions, which were shown in Table 22.

TABLE 20

Weight and Weight Percent of Each Component (Based on Total Solution Weight) for Three Oxybutynin HCl Transdermal Systems

|  | Oxy-P1 | Oxy-P2 | Oxy-P3 |
|---|---|---|---|
| Oxybutynin HCl | 0.5 g (6.5%) | 0.5 g (6.3%) | 0.5 g (6.2%) |
| DI water | 0.65 g (8.4%) | 0.75 g (9.5%) | 0.85 g (10.5%) |
| NaOH | 0.15 g (1.9%) | 0.25 g (3.2%) | 0.35 g (4.3%) |
| Propylene glycol | 0.3 g (3.9%) | 0.3 g (3.8%) | 0.3 g (3.7%) |
| Triton X100 | 0.1 g (1.3%) | 0.1 g (1.3%) | 0.1 g (1.2%) |
| PIB adhesive (30% solid) | 4 g (51.9%) | 4 g (50.6%) | 4 g (49.4%) |
| Methylal | 1 g (13.0%) | 1 g (12.7%) | 1 g (12.3%) |
| Heptane | 1 g (13.0%) | 1 g (12.7%) | 1 g (12.3%) |

TABLE 21

Weight and Theoretical Weight Percent of Each Component in the Dried Film for Three Oxybutynin HCl Transdermal Systems

|  | Oxy-P1 | Oxy-P2 | Oxy-P3 |
|---|---|---|---|
| Oxybutynin HCl | 0.5 g (15.4%) | 0.5 g (14.9%) | 0.5 g (14.5%) |
| NaOH | 0.15 g (4.6%) | 0.25 g (7.5%) | 0.35 g (10.1%) |
| Propylene glycol | 0.3 g (9.2%) | 0.3 g (9.0%) | 0.3 g (8.7%) |
| Triton X100 | 0.1 g (3.1%) | 0.1 g (3.0%) | 0.1 g (2.9%) |
| PIB adhesive | 1.2 g (36.9%) | 1.2 g (35.8%) | 1.2 g (34.8%) |
| Methylal | 1 g (30.8%) | 1 g (29.9%) | 1 g (29.0%) |

TABLE 22

Cumulative Amount of Oxybutynin HCl across human cadaver skin for Oxybutynin HCl Transdermal Systems ($\mu g/cm^2$)

|  | Oxy-P1 | Oxy-P2 | Oxy-P3 |
|---|---|---|---|
| 5 hours | 691.0 | 2108.7 | 1399.5 |
| 10.5 hours | 1259.4 | 2615.9 | 1865.9 |
| 24 hours | 1747.7 | 2853.5 | 2322.8 |

The cumulative amount of diclofenac sodium across human cadaver skin at 24 hours ranged from 1747.7 $\mu g/cm^2$ to 2322.8 $\mu g/cm^2$ when the NaOH concentration in the dried patch was increased from 4.6% to 10.1%.

We claim:

1. A method for enhancing the flux of a pharmacologically active agent comprised of a nitrogenous base through a body surface, comprising administering the active agent to a localized region of a human patient's body surface in combination with a hydroxide-releasing agent, the hydroxide-releasing agent applied to the body surface in a predetermined amount effective to enhance the flux of the active agent through the predetermined area of the body surface without causing damage thereto, and effective to provide a pH in the range of approximately 8.5 to 13.0 at the localized region of the body surface, during active agent administration, wherein the active agent and hydroxide-releasing agent are present in a formulation and the amount of hydroxide-releasing agent in the formulation applied to the body surface is the total of (a) the amount required to neutralize any acidic species in the formulation plus (b) an amount equal to approximately 0.5 wt. % to 25.0 wt. % of the formulation.

2. The method of claim 1, wherein the pH is in the range of approximately 8.5 to 11.

3. The method of claim 1, wherein the body surface is skin.

4. The method of claim 1, wherein the body surface is mucosal tissue.

5. The method of claim 1, wherein the formulation is aqueous.

6. The method of claim 5, wherein the formulation has a pH in the range of approximately 8.5 to 13.

7. The method of claim 6, wherein the pH is in the range of approximately 8.5 to 11.5.

8. The method of claim 1, wherein the active agent is an amine.

9. The method of claim 8, wherein the active agent is a primary amine.

10. The method of claim 8, wherein the active agent is a secondary amine.

11. The method of claim 8, wherein the active agent is a tertiary amine.

12. The method of claim 1, wherein the active agent is a nitrogen-containing heterocycle.

13. The method of claim 12, wherein the heterocycle is non-aromatic.

14. The method of claim 12, wherein the heterocycle is aromatic.

15. The method of claim 1, wherein the active agent is an azo compound.

16. The method of claim 1, wherein the active agent is an imine.

17. The method of claim 5, wherein the aqueous formulation is selected from the group consisting of a cream, a gel, a lotion, and a paste.

18. The method of claim 17, wherein the formulation is a cream.

19. The method of claim 17, wherein the formulation is a gel.

20. The method of claim 1, wherein the formulation is nonaqueous.

21. The method of claim 20, wherein the formulation is an ointment.

22. The method of claim 1, wherein the hydroxide-releasing agent releases free hydroxide ions in the presence of an aqueous fluid.

23. The method of claim 1, wherein the hydroxide-releasing agent is selected from the group consisting of inorganic hydroxides, inorganic oxides, metal salts of weak acids and mixtures thereof.

24. The method of claim 23, wherein the hydroxide-releasing agent is an inorganic hydroxide.

25. The method of claim 24, wherein the inorganic hydroxide is selected from the group consisting of ammonium hydroxide, alkali metal hydroxides, alkaline earth metal hydroxides, and mixtures thereof.

26. The method of claim 25, wherein the inorganic hydroxide is selected from the group consisting of ammonium hydroxide, sodium hydroxide, calcium hydroxide, potassium hydroxide, magnesium hydroxide, and mixtures thereof.

27. The method of claim 26, wherein the inorganic hydroxide is sodium hydroxide.

28. The method of claim 26, wherein the inorganic hydroxide is potassium hydroxide.

29. The method of claim 23, wherein the hydroxide-releasing agent is an inorganic oxide.

30. The method of claim 29, wherein the inorganic oxide is selected from the group consisting of magnesium oxide, calcium oxide, and mixtures thereof.

31. The method of claim 23, wherein the hydroxide-releasing agent is a metal salt of a weak acid.

32. The method of claim 31, wherein the hydroxide-releasing agent is selected from the group consisting of sodium acetate, sodium carbonate, tribasic sodium phosphate, dibasic sodium phosphate, sodium borate, potassium carbonate, potassium acetate, dibasic potassium phosphate, tribasic potassium phosphate, sodium metaborate, and mixtures thereof.

33. The method of claim 24, wherein the amount of inorganic hydroxide in the formulation is the total of (a) the amount required to neutralize any salts and acidic species in the formulation plus (b) an amount equal to approximately 0.5 wt. % to 4.0 wt. % of the formulation.

34. The method of claim 33, wherein the amount of inorganic hydroxide in the formulation is the total of (a) the amount required to neutralize any salts and acidic species in the formulation plus (b) an amount equal to approximately 0.5 wt. % to 3.0 wt. % of the formulation.

35. The method of claim 34, wherein the amount of inorganic hydroxide in the formulation is the total of (a) the amount required to neutralize any salts and acidic species in the formulation plus (b) an amount equal to approximately 0.75 wt. % to 2.0 wt. % of the formulation.

36. The method of claim 35, wherein the amount of inorganic hydroxide in the formulation is the total of (a) the amount required to neutralize any salts and acidic species in the formulation plus (b) an amount equal to approximately 1.0 wt. % of the formulation.

37. The method of claim 1, wherein the active agent is in the form of an acid addition salt, and the amount in (a) is the amount required to neutralize the acid addition salt and any other acidic species in the formulation.

38. The method of claim 29, wherein the formulation contains up to approximately 25 wt. % of the hydroxide-releasing agent.

39. The method of claim 38, wherein the formulation contains up to approximately 20 wt. % of the hydroxide-releasing agent.

40. The method of claim 31, wherein the formulation contains up to approximately 25 wt. % of the hydroxide-releasing agent.

41. The method of claim 40, wherein the formulation contains up to approximately 20 wt. % of the hydroxide-releasing agent.

42. The method of claim 1, wherein the active agent and hydroxide-releasing agent are administered by applying a drug delivery device to the localized region of the patient's body surface thereby forming a body surface-delivery device interface, the device comprising the active agent and the hydroxide-releasing agent, and having an outer backing layer that serves as the outer surface of the device during use.

43. The method of claim 42, wherein the active agent and hydroxide-releasing agent are present in an adhesive, gel or liquid formulation contained within the device.

44. The method of claim 42, wherein the outer backing layer is occlusive.

45. The method of claim 42, wherein the pH at the interface is in the range of approximately 8.5 to 11.5.

46. The method of claim 1, wherein the active agent is administered in combination with an additional permeation enhancer.

47. The method of claim 1, wherein the active agent is locally acting and administration is topical.

48. The method of claim 1, wherein the active agent is systemically acting and administration is transdermal.

49. The method of claim 1, wherein the active agent and the hydroxide-releasing agent are administered without any additional permeation enhancer.

50. A composition of matter useful for the delivery of a pharmacologically active agent through a body surface, comprising a formulation of:
    (a) a therapeutically effective amount of a pharmacologically active agent comprised of a nitrogenous base;
    (b) a hydroxide-releasing agent in an amount effective to enhance the flux of the active agent through the body surface without causing damage thereto and effective to provide a pH in the range of approximately 8.5 to 13.0 at the body surface, during active agent administration, and wherein the amount of hydroxide-releasing agent in the formulation applied to the body surface is the total of (a) the amount required to neutralize any acidic species in the formulation plus (b) an amount equal to approximately 0.5 wt. % to 25.0 wt. % of the formulation; and
    (c) a pharmaceutically acceptable carrier suitable for topical or transdermal active agent administration.

51. The composition of claim 50, wherein the pH is in the range of approximately 8.5 to 11.5.

52. The composition of claim 50, wherein the amount of hydroxide-releasing agent in the formulation is the total of (a) the amount required to neutralize any salts and acidic species in the formulation plus (b) an amount equal to approximately 0.5 wt. % to 4.0 wt. % of the formulation.

53. The composition of claim 52, wherein the amount of hydroxide-releasing agent in the formulation is the total of (a) the amount required to neutralize any salts and acidic species in the formulation plus (b) an amount equal to approximately 0.5 wt. % to 3.0 wt. % of the formulation.

54. The composition of claim 53, wherein the amount of hydroxide-releasing agent in the formulation is the total of (a) the amount required to neutralize any salts and acidic species in the formulation plus (b) an amount equal to approximately 0.75 wt. % to 2.0 wt. % of the formulation.

55. The composition of claim 54, wherein the amount of hydroxide-releasing agent in the formulation is the total of (a) the amount required to neutralize any salts and acidic species in the formulation plus (b) an amount equal to approximately 1.0 wt. % of the formulation.

56. The composition of claim 50, wherein the active agent is an amine.

57. The composition of claim 56, wherein the active agent is a primary amine.

58. The composition of claim 56, wherein the active agent is a secondary amine.

59. The composition of claim 56, wherein the active agent is a tertiary amine.

60. The composition of claim 50, wherein the active agent is a nitrogen-containing heterocycle.

61. The composition of claim 60, wherein the heterocycle is non-aromatic.

62. The composition of claim 60, wherein the heterocycle is aromatic.

63. The composition of claim 60, wherein the active agent is an azo compound.

64. The composition of claim 50, wherein the active agent is an imine.

65. A system for the transdermal administration of a pharmacologically active agent, comprising:
   (a) at least one drug reservoir containing (i) a pharmacologically active agent comprised of a nitrogenous base and (ii) a hydroxide-releasing agent in an amount effective to enhance the flux of the active agent through the body surface without causing damage thereto, and effective to provide a pH in the range of approximately 8.5 to 13.0 at the localized region of the body surface, during drug administration, wherein the amount of hydroxide-releasing agent in the reservoir is the total of (a) the amount required to neutralize any acidic species in the reservoir plus (b) an amount equal to approximately 0.5 wt. % to 25.0 wt. % of the reservoir;
   (b) a means for maintaining the system in active agent- and enhancer-transmitting relationship to the body surface; and
   (c) an occlusive backing layer that serves as the outer surface of the system during use.

66. The system of claim 65, wherein the drug reservoir is comprised of a polymeric adhesive.

67. The system of claim 66, wherein the polymeric adhesive serves as the means for maintaining the system in active agent and enhancer transmitting relationship to the body service.

68. The system of claim 65, wherein the drug reservoir is comprised of a hydrogel.

69. The system of claim 65, wherein the drug reservoir is comprised of a scaled pouch containing the active agent and hydroxide-releasing agent in a liquid or semi-solid formulation.

70. The system of claim 65, wherein the active agent is an amine.

71. The system of claim 70, wherein the active agent is a primary amine.

72. The system of claim 70, wherein the active agent is a secondary amine.

73. The system of claim 70, wherein the active agent is a tertiary amine.

74. The system of claim 65, wherein the active agent is a nitrogen-containing heterocycle.

75. The system of claim 74, wherein the heterocycle is non-aromatic.

76. The system of claim 74, wherein the heterocycle is aromatic.

77. The system of claim 65, wherein the active agent is an azo compound.

* * * * *

UNITED STATES PATENT AND TRADEMARK OFFICE
CERTIFICATE OF CORRECTION

PATENT NO. : 6,719,997 B2
DATED : April 13, 2004
INVENTOR(S) : Tsung-Min Hsu et al.

It is certified that error appears in the above-identified patent and that said Letters Patent is hereby corrected as shown below:

Column 32,
Line 64, please delete "60" and insert -- 50 --.

Signed and Sealed this

Twenty-seventh Day of July, 2004

JON W. DUDAS
*Acting Director of the United States Patent and Trademark Office*